United States Patent [19]

Wada et al.

[11] Patent Number: 4,904,460

[45] Date of Patent: Feb. 27, 1990

[54] PROCESS FOR PRODUCING MONOSILANE

[75] Inventors: Keisuke Wada; Junzo Haji; Ichiro Yokotake, all of Yokohama, Japan

[73] Assignee: Mitsubishi Kasei Corporation, Tokyo, Japan

[21] Appl. No.: 337,657

[22] Filed: Apr. 13, 1989

[30] Foreign Application Priority Data

Apr. 13, 1988 [JP]  Japan ................................. 63-91141
Apr. 13, 1988 [JP]  Japan ................................. 63-91142
Dec. 22, 1988 [JP]  Japan ................................. 63-324472

[51] Int. Cl.$^4$ ............................................. C01B 33/04
[52] U.S. Cl. ................................................... 423/347
[58] Field of Search .......................................... 423/347

[56] References Cited

U.S. PATENT DOCUMENTS

| | | |
|---|---|---|
| 4,016,188 | 4/1977 | Kotzsch et al. ...................... 423/347 |
| 4,613,491 | 9/1986 | Jung et al. ............................ 423/347 |
| 4,725,420 | 2/1988 | Tachikawa et al. ................. 423/347 |

FOREIGN PATENT DOCUMENTS

| | | | |
|---|---|---|---|
| 2247873 | 4/1973 | Fed. Rep. of Germany ...... | 423/347 |
| 059721 | 1/1975 | Japan ................................. | 423/347 |
| 0204815 | 11/1983 | Japan ................................. | 423/347 |
| 0062675 | 4/1984 | Japan ................................. | 423/347 |
| 059047 | 1/1985 | Japan ................................. | 423/347 |
| 2046913 | 2/1987 | Japan ................................. | 423/347 |

*Primary Examiner*—John Doll
*Assistant Examiner*—Lori F. Cuomo

*Attorney, Agent, or Firm*—Oblon, Spivak, McClelland, Maier & Neustadt

[57] ABSTRACT

A process for producing monosilane, which comprises disproportionating an alkoxysilane of the formula:

$$H_nSi(OR)_{4-n} \quad \text{(I)}$$

wherein R is an alkyl group having from 1 to 6 carbon atoms or a cycloalkyl group and n is an integer of 1, 2 or 3, in the presence of a catalyst, wherein the catalyst comprises at least one compound selected from the group consisting of aromatic alkoxides of the formula:

$$MOAr \quad \text{(II)}$$

wherein M is a metal of Group Ia of the Periodic Table and Ar is a substituted or unsubstituted aromatic hydrocarbon group, and quaternary ammonium and phosphonium compounds of the formula:

$$R^1R^2R^3R^4ZX \quad \text{(III)}$$

wherein each of $R^1$, $R^2$, $R^3$ and $R^4$ which may be the same or different, is a substituted or unsubstituted alkyl or aryl group, Z is a nitrogen atom or a phosphorus atom and X is an anion.

17 Claims, No Drawings

PROCESS FOR PRODUCING MONOSILANE

The present invention relates to a process for producing monosilane. More particularly, the present invention relates to a catalyst and a solvent whereby disproportionation of an alkoxysilane can efficiently be conducted.

Monosilane is a gas having a boiling point of −112° C. When heated at a temperature of e.g. at least 900° C., it decomposes into silicon and hydrogen, whereby silicon of a high purity can be obtained.

Several methods have been known for the production of such monosilane, including a method wherein magnesium silicide is decomposed by hydrochloric acid, and a method wherein a silicon halide is reduced. One of them is a method of disproportionating an alkoxysilane. In this method, the starting material contains no halogen, whereby monosilane of a high purity free from halogen can be obtained.

Japanese Examined Patent Publications No. 20040/1976 and No. 20440/1976 disclose a process for producing a silane of the formula $Si_nH_{2n+2}$, which comprises decomposing an alkoxysilane of the formula $H_nSi(OR)_{4-n}$ wherein n is an integer of 1, 2 or 3, in the presence of an alkyl alcoholate. Specifically, they disclose a process wherein triethoxysilane is decomposed into monosilane and tetraethoxysilane in the presence of sodium ethylate. This process has a feature that it is thereby possible to produce monosilane with high selectivity. However, the activity of the catalyst is insufficient, and a large amount of the catalyst is required to improve the conversion of the alkoxysilane as the starting material.

Japanese Unexamined Patent Publication No. 41321/1974 discloses a process for producing monosilane and a lower silane ester by disproportionating a hydrogen silane ester in the presence of a catalyst comprising an element of Group Ia, IIa, IIb, IIIa or IIIb of the Periodic Table, or iron or manganese, or comprising an organic nitrogen compound. This disproportionating catalyst includes a wide range of compounds. However, actually catalyst used for the disproportionation reaction are limited to a metal acetylacetonate (the metal is magnesium, iron, aluminum or zinc), hexamethylphosphoric triamide, sodium tert-butylate and lithium chloride. The catalytic activities are not necessarily sufficient.

It is an object of the present invention to produce monosilane efficiently from alkoxysilane as a starting material.

Another object of the present invention is to obtain a by-product tetraalkoxysilane with high selectivity.

To accomplish such objects, the present invention provides a process for conducting a disproportionation reaction in the presence of a certain specific catalyst. Further, the present invention provides a process for conducting a disproportionation reaction in the presence of a certain specific solvent.

The present invention provides a process for producing monosilane, which comprises disproportionating an alkoxysilane of the formula:

$$H_nSi(OR)_{4-n} \tag{I}$$

wherein R is an alkyl group having from 1 to 6 carbon atoms or a cycloalkyl group having up to 6 carbon atoms and n is an integer of 1, 2 or 3, in the presence of a catalyst, wherein the catalyst comprises at least one compound selected from the group consisting of aromatic alkoxides of the formula:

$$MOAr \tag{II}$$

wherein M is a metal of Group Ia of the Periodic Table and Ar is a substituted or unsubstituted aromatic hydrocarbon group, and quaternary ammonium and phosphonium compounds of the formula:

$$R^1R^2R^3R^4ZX \tag{III}$$

wherein each of $R^1, R^2, R^3$ and $R^4$ which may be the same or different, is a substituted or unsubstituted alkyl or aryl group, Z is a nitrogen atom or a phosphorus atom and X is an anion.

The present invention also provides a process for producing monosilane, wherein the above disproportionation reaction is conducted in the presence of a nitrogen-containing or sulfur-containing aprotic polar solvent. Now, the present invention will be described in detail with reference to the preferred embodiments.

The starting material alkoxysilane useful in the present invention is represented by the formula I:

$$H_nSi(OR)_{4-n} \tag{I}$$

The alkyl group for R includes methyl, ethyl, propyl and hexyl, the cycloalkyl group for R includes cyclohexyl, and n is an integer of from 1 to 3.

The disproportionation reaction of the present invention is considered to proceed in accordance with the following formula to give monosilane and tetraalkoxysilane as the final products:

$$2H_nSi(OR)_{4-n} \rightarrow$$
$$H_{n+1}Si(OR)_{4-n-1} + H_{n-1}Si(OR)_{4-n+1}$$

Thus, as the starting material, $H_nSi(OR)_{4-n}$ wherein n is an integer of from 1 to 3 is useful, whereby the corresponding various halogenated alkoxysilanes are obtainable as products of the disproportionation reaction.

However, a hydrogenated alkoxysilane whereby n is 3 or 2, is unstable. Accordingly, it is practically difficult to use it alone as the starting material or to obtain it as a product. In the process of the present invention, it is preferred to employ a trialkoxysilane easy to handle such as trimethoxysilane or triethoxysilane to obtain monosilane and a tetraalkoxysilane as the products.

The alkoxysilane used as the starting material, may not necessarily be pure. For example, it may be a mixture of a trialkoxysilane and a tetraalkoxysilane. The alkoxysilane of the formula I can be prepared by various processes. However, an alkoxysilane obtainable by reacting metal silicon and an alcohol in accordance with the following formula is particularly preferred since it contains no substantial impurities containing halogens.

$$Si + mROH \rightarrow H_{4-m}Si(OR)_m + (m-2)H_2$$

The disproportionation reaction of the present invention is conducted in the presence of a catalyst which comprises at least one compound selected from the group consisting of the aromatic alkoxides of the formula II and the quaternary ammonium and phosphonium salts of the formula III.

MOAr                                    (II)

In the formula, M is a metal of Group Ia of the Periodic Table. Specifically, M may be lithium, sodium, potassium, rubidium, cesium or francium, preferably sodium or potassium. Ar is a substituted or unsubstituted aromatic hydrocarbon group. As the substituent, an amino group, a nitro group, a halogen atom, a hydroxyl group, an alkoxy group or a phenoxy group, may be mentioned. Specifically, Ar may be an unsubstituted aromatic hydrocarbon group such as phenyl, α- or β-naphthyl, o-tolyl, m-tolyl, or p-tolyl, or an aromatic hydrocarbon group substituted by an amino group, a nitro group, a halogen atom, a hydroxyl group, a methoxy group or a phenoxy group, such as o-aminophenyl, m-aminophenyl, p-aminophenyl, o-nitrophenyl, m-nitrophenyl, p-nitrophenyl, o-chloropehnyl, m-chlorophenyl, p-chlorophenyl, o-hydroxyphenyl, m-hydroxyphenyl, p-hydroxyphenyl, o-methoxyphenyl, m-methoxyphenyl, p-methoxyphenyl, o-phenoxyphenyl, m-phenoxyphenyl or p-phenoxyphenyl. Preferred is a phenyl group.

Specific examples of MOAr include lithium phenoxide, sodium phenoxide, potassium phenoxide, cesium phenoxide, sodium o-methylphenoxide, sodium m-methylphenoxide, sodium p-methylphenoxide, sodium o-aminophenoxide, sodium m-aminophenoxide, sodium p-aminophenoxide, sodium o-nitrophenoxide, sodium m-nitrophenoxide, sodium p-nitrophenoxide, sodium o-chlorophenoxide, sodium m-chlorophenoxide, sodium p-chlorophenoxide, sodium o-methoxyphenoxide, sodium m-methoxyphenoxide, sodium p-methoxyphenoxide, sodium o-phenoxyphenoxide, sodium m-phenoxyphenoxide, sodium p-phenoxyphenoxide, monosodium catechol, disodium catechol, monosodium resorcinol, disodium resorcinol, monosodium hydroquinone and disodium hydroquinone. Usually sodium phenoxide or potassium phenoxide is preferably used.

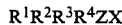
$R^1R^2R^3R^4ZX$                          (III)

In the formula, each Of $R^1$ to $R^4$ which may be the same or different, is an alkyl group or an aryl group, Z is a nitrogen atom or a phosphorus atom, and X is an anion.

Each Of $R^1$ to $R^4$ may be a substituted or unsubstituted alkyl group such as methyl, ethyl, propyl, butyl, decyl or benzyl. Preferred is a $C_1$–$C_4$ alkyl group. Or, each of $R^1$ to $R^4$ is a substituted or unsubstituted aryl group such as phenyl or tolyl. X is an anion such as a fluoride ion, a chloride ion, a bromide ion, an iodide ion, a hydroxyl ion, an acetic acid ion. Preferred is a hydroxyl ion or an acetic acid ion.

Specific examples of the quaternary ammonium salt include tetramethylammonium chloride, tetramethylammonium bromide, tetramethylammonium iodide, tetramethylammonium acetate, tetramethylammonium hydroxide, tetrabutylammonium chloride, tetrabutylammonium bromide, tetrabutylammonium iodide, tetrabutylammonium acetate, tetrabutylammonium hydroxide, trimethylbenzylammonium chloride, trimethylbenzylammonium bromide, trimethylbenzylammonium iodide, trimethylbenzylammonium acetate, trimethylbenzylammonium hydroxide, trimethylphenylammonium chloride, trimethylphenylammonium bromide, trimethylphenylammonium iodide, trimethylphenylammonium acetate and trimethylbenzylammonium hydroxide.

Specific examples of the quaternary phosphonium salt include tetramethylphosphonium chloride, tetramethylphosphonium bromide, tetramethylphosphonium iodide, tetramethylphosphonium acetate, tetramethylphosphonium hydroxide, tetrabutylphosphonium chloride, tetrabutylphosphonium bromide, tetrabutylphosphonium iodide, tetrabutylphosphonium acetate, tetrabutylphosphonium hydroxide, trimethylbenzylphosphonium chloride, trimethylbenzylphosphonium bromide, trimethylbenzylphosphonium iodide, trimethylbenzylphosphonium acetate, trimethylbenzylphosphonium hydroxide, trimethylphenylphosphonium chloride, trimethylphenylphosphonium bromide, trimethylphenylphosphonium iodide, trimethylphenylphosphonium acetate and trimethylphenylphosphonium hydroxide.

The catalyst may be used in an amount of at least 0.001% by weight relative to the starting material, alkoxysilane. However, it is usually used in an amount within a range of from 0.01 to 50% by weight, preferably from 0.01 to 10% by weight.

The reaction may be conducted in a batch system or a continuous system.

The alkoxysilane as a starting material is liquid at room temperature. Therefore, a solvent is not necessarily required for the reaction. However, it is preferred to conduct the reaction in a homogeneous system by using a solvent, as the case requires. As the solvent for the reaction, various types may be employed including hydrocarbons such as hexane, cyclohexane and benzene; ethers such as tetrahydrofuran; and tetraalkoxysilanes such as tetramethoxysilane and tetraethoxysilane. Among them, aprotic polar solvents are preferred. The present inventors have found that among aprotic polar solvents, it is particularly preferred to use a nitrogen-containing compound or a sulfur-containing compound as the solvent. The nitrogen-containing aprotic polar solvent provides a good solubility to the catalyst and serves to increase the catalytic activities, thus contributing to the efficiency of the reaction. Whereas, when the sulfur-containing aprotic polar solvent is used, oligomerization of a tetraalkoxysilane as a by-product can be depressed, whereby the selectivity for the tetraalkoxysilane as a useful by-product can be improved.

The nitrogen-containing aprotic polar solvent includes amides such as N,N-dimethylformamide, N,N-dimethylacetamide, N methyl-2 pyrrolidone and 1,3-dimethyl-2-imidazolidone; nitriles such as acetonitrile and propionitrile; nitro compounds such as nitrobenzene and nitromethane. Particularly preferred are N-methyl-2-pyrrolidone, N,N dimethylacetamide, N,N-dimethylformamide, 1,3-dimethyl-2-imidazolidone and acetonitrile. The sulfur-containing aprotic polar solvent includes dimethylsulfoxide and sulfolane. Particularly preferred is dimethylsulfoxide.

The solvent is used in an amount of from 0.1 to 100 parts by weight, usually from 0.5 to 10 parts by weight, relative to the alkoxysilane of the formula I.

The solvent may be a single solvent or a solvent mixture such as a mixture of sulfur-containing compounds or a mixture of a nitrogen-containing compound with other solvent such as benzene or a tetraalkoxysilane such as tetramethoxysilane or tetraethoxysilane.

The disproportionation reaction may be conducted by a batch system or a continuous system.

The reaction pressure may be at any level ranging from a reduced pressure to an elevated pressure. However, the product monosilane is inflammable upon contact with air. Therefore, the reaction is preferably conducted under an atmospheric pressure condition.

The reaction may adequately be conducted at room temperature. However, it is usually preferred to conduct the reaction at a temperature of from 30 to 80° C. under heating.

The reaction is usually conducted in an inert gas atmosphere such as nitrogen or argon.

The monosilane (boiling point: −112° C.) formed by the reaction is withdrawn together with the inert gas such as nitrogen or argon. Therefore, if necessary such a gas mixture is subjected to separation treatment such as deep cooling separation to separate out the inert gas to recover the monosilane. The monosilane thus obtained may further be purified by a conventional method such as a multi-stage deep cooling separation or adsorption treatment by means of zeolite or active carbon.

On the other hand, in the reaction solution, a tetraalkoxysilane is present as another product (by-product) of the disproportionation reaction. After completion of the reaction, the reaction solution may be subjected to distillation to separate and recover the tetraalkoxysilane and the solvent, respectively.

The monosilane obtained by the process of the present invention is useful as a starting material for producing high purity silicon for semi-conductors, or as a starting material for amorphous silicon light-sensitive materials, solar cells or new ceramic materials.

On the other hand, the tetraalkoxysilane is useful as a starting material for high purity silica or synthetic quartz, or it is useful for various purposes, for example as a binder for casting molds. The process of the present invention has a merit that the obtained monosilane and tetraalkoxysilane are not contaminated by halogen, since no halide is used in the process.

Now, the present invention will be described in further detail with reference to Examples. However, it should b understood that the present invention is by no means restricted to such specific Examples.

EXAMPLE 1

Into a SUS-316 autoclave equipped with a nitrogen gas supply tube, a condenser-equipped gas discharge tube and a liquid feed tube and having an internal capacity of 100 ml., a teflon stirrer and 5 mg of sodium phenoxide were charged, and the interior of the autoclave was thoroughly flushed with nitrogen. From the liquid feed tube, 25 g. of N-methyl-2-pyrrolidone was introduced into the autoclave, and the autoclave was heated to 40° C. Then, 4.89 g. (40.0 mmol.) of trimethoxysilane was introduced from the liquid feed tube, and the mixture was stirred by the magnetic stirrer. Upon contact of the catalyst with the trimethoxysilane, the reaction started to form monosilane. The formed monosilane was withdrawn together with nitrogen gas and quantitatively analyzed by gas chromatography as time passed. The reaction was conducted at 40° C. for two hours, whereby the conversion of the trimethoxysilane was 100%, and the amount of the formed monosilane was 10.0 mmol.

Further, after completion of the reaction, the reaction solution was analyzed by gas chromatography to ascertain the formation of 25.9 mmol. of tetramethoxysilane, 1.8 mmol. of hexamethoxydisiloxane as a dimer, and 0.15 mmol. of octamethoxytrisiloxane as a trimer.

COMPARATIVE EXAMPLE 1

Into the same autoclave as used in Example 1, 44 mg. of sodium methoxide was charged, the autoclave was thoroughly flushed with nitrogen gas, 4.89 g. (40.0 mmol.) of trimethoxysilane was then introduced, and the reaction was conducted in the same manner as in Example 1 without using N-methyl-2-pyrrolidone. To hours later, the conversion of the trimethoxysilane was 75.8%, and the amount of the formed monosilane was 7.58 mmol.

COMPARATIVE EXAMPLE 2

Into the same autoclave as used in Example 1, 44 mg. of sodium methoxide, 25 g. of N-methyl-2-pyrrolidone and 4.89 g. (40.0 mmol.) of trimethoxysilane were charged, and the reaction was conducted in the same manner as in Example 1. Two hours later, the conversion of the trimethoxysilane was 83.6%, and the amount of the formed monosilane was 8.36 mmol.

EXAMPLE 2

The reaction was conducted in the same manner as in Example 1 except that 5 mg. of potassium phenoxide was used instead of sodium phenoxide, whereby the conversion of the trimethoxysilane was 100%, and the amount of the formed monosilane was 10.0 mmol.

EXAMPLE 3

The reaction was conducted in the same manner as in Example 1 except that 5 mg. of tetrabutylammonium acetate was used instead of sodium phenoxide, whereby the conversion of the trimethoxysilane was 100%, and the amount of the formed monosilane was 10.0 mmol.

EXAMPLE 4

The reaction was conducted in the same manner as in Example 3 except that 5 mg. of tetramethylammonium acetate was used instead of the tetrabutylammonium acetate, whereby the conversion of the trimethoxysilane was 100%, and the amount of the formed monosilane was 10.0 mmol.

EXAMPLE 5

The reaction was conducted in the same manner as in Example 3 except that 5 mg. of tetrabutylphosphonium acetate was used instead of the tetrabutylammonium acetate, whereby the conversion of the trimethoxysilane was 100%, and the amount of the formed monosilane was 8.62 mmol.

EXAMPLE 6

Into a SUS-316 autoclave equipped with a nitrogen gas supply tube, a condenser-equipped discharge tube and a liquid feed tube and having an internal capacity of 100 ml., a teflon stirrer and 5 mg. of sodium phenoxide were charged, and the interior of the autoclave was throughly flushed with nitrogen. From the liquid feed tube, 25 g. of dimethylsulfoxide was introduced into the autoclave, and the autoclave was heated to 40° C. Then, 4.89 g. (40.0 mmol.) of trimethoxysilane was introduced from the liquid feed tube, and the mixture was reacted at 40° C. for two hours in the same manner as in Example 1. Formed monosilane was withdrawn together with nitrogen gas and quantitatively analyzed by gas chromatography as time passed, whereby the conversion of the trimethoxysilane was 100%, and the amount of the formed monosilane was 10.0 mmol. After completion of the reaction, the reaction mixture was analyzed by gas chromatography to ascertain the formation of 28.4 mmol. of tetramethoxysilane, 0.7 mmol. of hexamethoxydisiloxane and 0.07 mmol. of octamethoxytrisiloxane.

EXAMPLE 7

The reaction was conducted in the same manner as in Example 1 except that 5 mg. of sodium phenoxide was used as the catalyst and 25 g. of acetonitrile was used as the solvent. Two hours later, the conversion of the trimethoxysilane was 100%, and the amount of the formed monosilane was 9.37 mmol.

EXAMPLE 8

The reaction was conducted in the same manner as in Example 7 except that 25 g. of dimethylformamide was used as the solvent. Two hours later, the conversion of the trimethoxysilane was 100%, and the amount of the formed monosilane was 9.81 mmol.

We claim:

1. A process for producing a monosilane, which consists essentially of:

disproportionating an alkoxysilane of the formula:

$$H_nSi(OR)_{4-n} \qquad (I)$$

wherein R is an alkyl group having from 1 to 6 carbon atoms or a cycloalkyl group having up to 6 carbon atoms and n is an integer of 1, 2 or 3, in the presence of a catalyst, said catalyst comprising at least one compound selected from the group consisting of aromatic alkoxides of the formula: MOAr (II) wherein M is a metal of group Ia of the Peirodic Table and Ar is a substituted or unsubstituted aromatic hydrocarbon group, quaternary ammonium compounds of the formula $R^1R^2R^3R^4NX$ or phosphonium compounds of the formula: $R^1R^2R^3R^4PX$ wherein each of $R^1$ through $R^4$, which may be the same or different, is a substituted or unsubstituted alkyl or aryl group and X is an anion.

2. The process according to claim 1, wherein in the alkoxysilane of the formula I, n is 1, R is an alkyl group having from 1 to 4 carbon atoms.

3. The process according to claim 1, wherein the alkoxysilane of the formula I is trimethoxysilane or triethoxysilane.

4. The process according to claim 1, wherein the catalyst is selected from the group consisting of the aromatic alkoxides of the formula II.

5. The process according to claim 4, wherein the catalyst is sodium phenoxide or potassium phenoxide.

6. The process according to claim 1, wherein the catalyst is selected from the group consisting of said quaternary ammonium and phosphonium compounds.

7. The process according to claim 6, wherein the catalyst is a quaternary ammonium compound of the formula:

$$(R)_4NX^1 \qquad (III-1)$$

wherein R is an alkyl group having from 1 to 4 carbon atoms and $X^1$ is a halogen ion, a hydroxyl ion or an acetic acid ion.

8. The process according to claim 7, wherein the quaternary ammonium compound is a tetramethylammonium salt or a tetrabutylammonium salt.

9. The process according to claim 6, wherein the catalyst is a quaternary phosphonium compound of the formula:

$$(R^5)_4PX^2 \qquad (III-2)$$

wherein $R^5$ is an alkyl group having from 1 to 5 carbon atoms and $X^2$ is a halogen ion, a hydroxyl ion or an acetic acid ion.

10. The process according to claim 1, wherein the disproportionation reaction is conducted in the presence of an aprotic polar solvent.

11. The process according to claim 10, wherein the aprotic polar solvent is a nitrogen-containing aprotic polar solvent.

12. The process according to claim 11, wherein the nitrogen-containing aprotic polar solvent is at least one member selected from the group consisting of amides, nitriles and nitro compounds.

13. The process according to claim 12, wherein the nitrogen-containing aprotic polar solvent is selected from the group consisting of N,N-dimethylformamide, N,N-dimethylacetamide, acetonitrile, N-methyl-2-pyrrolidone and 1,3-dimethyl-2-imidazolidone.

14. The process according to claim 10, wherein the aprotic polar solvent is a sulfur-containing aprotic solvent.

15. The process according to claim 14, wherein the sulfur-containing aprotic polar solvent is selected from the group consisting of sulfoxides and sulfolanes.

16. The process according to claim 15, wherein the sulfur-containing aprotic polar solvent is dimethyl sulfoxide.

17. A process for producing a monosilane, which consists essentially of:

disproportionating an alkoxysilane of the formula:

$$H_nSi(OR)_{4-n} \qquad (I)$$

wherein R is an alkyl group having from 1 to 6 carbon atoms or a cycloalkyl group having up to 6 carbon atoms and n is an integer of 1, 2 or 3, in the presence of a catalyst, said catalyst comprising at least one compound selected from the group consisting of aromatic alkoxides of the formula: MOAr (II) wherein M is a metal of group Ia of the Periodic Table and Ar is a substituted or unsubstituted aromatic hydrocarbon group, quaternary ammonium compounds of the formula $R^1R^2R^3R^4NX$ or phosphonium compounds of the formula: $R^1R^2R^3R^4PX$ wherein each or $R^1$ through $R^4$, which may be the same or different, is a substituted or unsubstituted alkyl or aryl group and X is an anion; and purifying the monosilane produced.

* * * * *